(12) United States Patent
Bennett et al.

(10) Patent No.: US 12,042,398 B2
(45) Date of Patent: *Jul. 23, 2024

(54) INTERBODY STANDALONE INTERVERTEBRAL IMPLANT

(71) Applicant: GLOBUS MEDICAL, INC., Audubon, PA (US)

(72) Inventors: Jeff Bennett, Pottstown, PA (US); William Rhoda, Media, PA (US); Sean Suh, Milltown, NJ (US); Daniel Davenport, Collegeville, PA (US); Duncan Sibson, Malvern, PA (US); Andrew Iott, Newtown Square, PA (US); Nick Padovani, Wynnewood, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/666,680

(22) Filed: Feb. 8, 2022

(65) Prior Publication Data

US 2022/0151802 A1    May 19, 2022

Related U.S. Application Data

(63) Continuation of application No. 16/412,473, filed on May 15, 2019, now Pat. No. 11,273,049, which is a
(Continued)

(51) Int. Cl.
*A61F 2/44* (2006.01)
*A61F 2/30* (2006.01)

(52) U.S. Cl.
CPC ........ *A61F 2/4455* (2013.01); *A61F 2/30744* (2013.01); *A61F 2/44* (2013.01); *A61F 2/4465* (2013.01); *A61F 2002/30014* (2013.01); *A61F 2002/30131* (2013.01); *A61F 2002/30387* (2013.01); *A61F 2002/30448* (2013.01); *A61F 2002/30563* (2013.01); *A61F 2002/30593* (2013.01); *A61F 2002/30604* (2013.01); *A61F 2002/30787* (2013.01); *A61F 2002/30836* (2013.01)

(58) Field of Classification Search
None
See application file for complete search history.

(56) References Cited

U.S. PATENT DOCUMENTS

| 7,135,043 B2 | 11/2006 | Nakahara et al. |
| 2002/0099376 A1 | 7/2002 | Michelson |

(Continued)

FOREIGN PATENT DOCUMENTS

| CA | 2389236 A1 | 12/2011 |
| JP | 2010538683 A | 12/2010 |

(Continued)

*Primary Examiner* — Tessa M Matthews

(57) ABSTRACT

Stand-alone interbody fusion devices and corpectomy devices suitable for use with an oblique implantation. The stand-alone interbody fusion devices may include a spacer having a substantially U-shaped body and a plate coupled to the spacer. The overall shape of the implant is asymmetrical such that a median plane, an oblique plane, or both planes divide the spacer and the plate into two asymmetrical halves. The implants are shaped and configured to allow for an oblique or anterolateral approach to the spine or an oblique corpectomy.

17 Claims, 8 Drawing Sheets

Related U.S. Application Data continuation of application No. 14/190,967, filed on Feb. 26, 2014, now Pat. No. 10,322,006.

(60) Provisional application No. 61/789,673, filed on Mar. 15, 2013.

(56) References Cited

U.S. PATENT DOCUMENTS

| | | | |
|---|---|---|---|
| 2007/0233253 A1* | 10/2007 | Bray | A61F 2/4455 623/17.11 |
| 2009/0105832 A1* | 4/2009 | Allain | A61F 2/4465 623/17.11 |
| 2009/0275988 A1 | 11/2009 | Baynham | |
| 2010/0057206 A1 | 3/2010 | Duffield et al. | |
| 2010/0087925 A1 | 4/2010 | Kostuik et al. | |
| 2010/0280619 A1* | 11/2010 | Yuan | A61F 2/4684 623/17.16 |
| 2010/0312345 A1* | 12/2010 | Duffield | A61F 2/4455 623/17.16 |
| 2012/0010472 A1 | 1/2012 | Spann | |
| 2012/0277867 A1* | 11/2012 | Kana | A61F 2/4455 623/17.16 |
| 2012/0277872 A1 | 11/2012 | Kana et al. | |
| 2013/0053894 A1* | 2/2013 | Gamache | A61B 17/7062 606/279 |
| 2013/0060339 A1 | 3/2013 | Duffield et al. | |
| 2013/0073047 A1* | 3/2013 | Laskowitz | A61F 2/447 623/17.16 |

FOREIGN PATENT DOCUMENTS

| | | |
|---|---|---|
| JP | 2012501744 A | 1/2012 |
| WO | 2008149223 A2 | 12/2008 |
| WO | 2012040268 A2 | 3/2012 |

* cited by examiner

INTERBODY STANDALONE INTERVERTEBRAL IMPLANT

CROSS-REFERENCE TO RELATED APPLICATIONS

This application is a continuation of U.S. patent application Ser. No. 16/412,473 filed on May 15, 2019 which is a continuation of U.S. patent application Ser. No. 14/190,967, filed on Feb. 26, 2014, which claims priority to provisional application No. 61/789,673 filed Mar. 15, 2013. This application also cross-references U.S. Pat. No. 8,328,872, which issued Dec. 11, 2012. The entire contents of both documents are incorporated herein by reference in their entirety for all purposes.

FIELD OF THE INVENTION

The present disclosure generally relates to fixation devices for positioning and immobilizing adjacent vertebral bodies and corpectomy devices. In particular, the devices may include stand-alone interbody fusion and oblique corpectomy devices containing at least one spacer and at least one plate.

BACKGROUND OF THE INVENTION

As people age, the intervertebral discs in the spinal column may start to deteriorate. Subsequently, the intervertebral discs being to lose height. As a result of the loss of height between vertebral bodies, the nerves exiting from the spinal canal become compressed and pinched, which causes pain among other neurological deficits. One solution is to insert a spacer in place of the disc to restore the height and to promote fusion between adjacent vertebral bodies to permanently maintain the height restoration. Additional fixation is also needed to stabilize the spinal segment. A plate is usually provided, the plate being positioned on the anterior portions of the adjacent vertebral bodies. In some cases, the profile of the plate becomes obstructive to the anatomy. The approach to the spine is also significant in that a direct anterior approach requires navigation or dissection of vascular anatomy. As a result, there is a need to incorporate the plate and the spacer into one device, to limit any profile protruding out of the spine column, and to avoid proximal anatomy from a direct anterior approach. With regard to corpectomy devices, there is a similar need for access to perform the corpectomy and suitable devices to replace at least a portion of damaged or collapsed vertebrae.

SUMMARY OF THE INVENTION

To meet this and other needs, stand-alone interbody fusion implants and corpectomy implants suitable for an oblique or anterolateral approach to the spine or for use with an oblique corpectomy are provided. The shape and configuration of the implants are particularly suitable for an oblique or anterolateral approach to the spine due to the asymmetrical nature of the implant design. The multi-component spacer and plate are also contained within the disc space to provide for a low or zero profile with respect to the anterior and lateral aspects of the spinal column. Thus, the plate and spacer are incorporated into a single device and any profile protruding out of the spinal column is limited.

According to one embodiment, an intervertebral implant for implantation in an intervertebral space between adjacent vertebrae includes a spacer and a plate. The spacer has a substantially U-shaped body, a superior surface, an inferior surface, a first end, and a second end. The inferior and superior surfaces each have a contact area configured to engage adjacent vertebrae. The plate has an upper surface, a lower surface, a first end, a second end, an anterior surface, and at least one hole traversing the plate for receiving a fastener (e.g., a screw). The plate is coupled to the spacer where the first end of the spacer engages the first end of the plate and the second end of the spacer engages the second end of the plate. The implant is asymmetrical such that a median plane divides the spacer and the plate into two asymmetrical halves. In addition or in the alternative, the implant may be asymmetrical such that an oblique plane divides the spacer and the plate into two asymmetrical halves.

The asymmetrical nature of the implant may allow for an oblique or anterolateral approach to the spine (e.g., lumbar, cervical). In particular, the implant may be inserted in an oblique direction, e.g., at an angle of about 45° with respect to the mid-sagittal plane. By providing this oblique or anterolateral approach, no dissection of the vessels in front of the vertebrae is required. Thus, the vascular anatomy of the patient may be avoided. In addition, when fully inserted, the implant may be contained within the disc space to provide for a low or zero profile design in regard to the anterior and lateral aspects of the spinal column.

The implant may be asymmetrical in a number of different ways. The spacer has a substantially U-shaped body, which may be asymmetrical along the median plane, the oblique plane, or both planes. The plate may have a curved body, which also may be asymmetrical along the median plane, the oblique plane, or both planes. Thus, the plate, the spacer, or both of the plate and the spacer may be independently asymmetrical. The plate may be asymmetrical along the oblique plane where the first end of the plate extends a distance beyond the second end of the plate or vice versa. Similarly, the spacer may be asymmetrical along the oblique plane where the second end of the spacer extends a distance beyond the first end of the spacer or vice versa. The spacer may further include a leading taper. The leading taper may be located along the insertion direction of the implant, which in the case of an oblique direction may allow for the leading taper to be positioned asymmetrically on the spacer. For example, the leading taper may be asymmetrically positioned such that the leading taper crosses or intersects the oblique plane.

The spacer and the plate may be coupled or connected together in any suitable manner. In one embodiment, the first and second ends of the plate and the first and second ends of the spacer each comprise first and second projections with a recess defined therebetween. The first projections of the spacer may include a sloped upper surface which corresponds to a sloped lower surface of the first projections of the plate. At least one of the first and second projections of the plate or the spacer is matingly received in the corresponding recess of the plate or the spacer. For example, the second projections of the plate may be dovetailed or friction fit within the recesses of the spacer. In addition or in the alternative, the spacer and the plate may be secured together with pins.

The plate of the implant may include one or more bores or through holes designed to accommodate fixation devices or fasteners, such as screws. The anterior surface may include one or more eyebrows projecting past the upper or lower surfaces which accommodate the locations of the through holes. The holes for receiving fasteners, such as screws may traverse the anterior surface of the plate at an angle divergent to a horizontal plane in order to secure the implant to one or both of the adjacent vertebrae. The implant may also include a locking mechanism disposed on the plate for preventing back out of the screws. For example, a cam-style blocking mechanism may be used with screws that capture the fixation device screws once they are inserted fully into the plate.

Unlike traditional spacers, which may contain one or more graft retaining areas where the spacer completely surrounds or envelops the graft retaining area, the spacer is substantially U-shaped with an open portion. When the spacer and plate are coupled together, the spacer and the plate together define an open graft area. In other words, the perimeter of the U-shaped spacer and the perimeter of the plate define an open area. The open graft area may extend from the superior surface to the inferior surface of the spacer. The opening may be configured for receiving bone graft material to promote fusion of the adjacent vertebral bodies. The spacer may also include a plurality of protrusions on the contact areas of the superior and inferior surfaces for engaging the adjacent vertebrae.

The plate and the spacer may be formed from any suitable biocompatible materials. For example, the plate may be manufactured from a biocompatible metal, such as titanium, for example. The spacer also may be manufactured from any suitable material, such as a biocompatible plastic, like polyether ether ketone (PEEK), for example.

According to another embodiment, a multi-level corpectomy implant for implantation in at least a portion of at least one vertebrae and in an intervertebral space between adjacent vertebrae includes a spacer. The spacer has a superior surface, an inferior surface, a first lateral surface, a second lateral surface, a front surface, and a rear surface. The first and second lateral surfaces each have at least one contact area configured to engage a portion of the vertebrae exposed by a corpectomy. The spacer is also configured to extend between at least two adjacent vertebrae. The spacer is shaped and configured to allow for an oblique or anterolateral approach.

The spacer may include at least one attachment mechanism to secure the spacer to the portion of the vertebrae exposed by the corpectomy. For example, the attachment mechanism may include one or more fasteners, screws, pins, or the like. In addition or in the alternative, the attachment mechanism may include a plurality of protrusions on the contact areas of the first and second lateral surfaces for engaging the portion of the vertebrae exposed by the corpectomy.

The multi-level corpectomy implant may also include one or more plates. The plate may be coupled to a portion of the front surface of the spacer. The plate has an anterior surface and at least one hole traversing through the anterior surface for receiving a fastener, such as a screw to secure the plate to one of the adjacent vertebrae. The implant may include two plates: a first plate coupled to a first portion of the front surface of the spacer and a second plate coupled to a second portion of the front surface of the spacer. The first plate may secure the spacer to a first vertebral body and the second plate may secure the spacer to a second vertebral body adjacent to the first vertebral body, for example, using one or more screws.

The plate and spacer may be comprised of any suitable material. For example, the spacer may be formed from a flexible elastomer. The spacer may also include a multi-component body including a biocompatible plastic and a flexible elastomer. The spacer may include a multi-component body including a first cage made from a biocompatible plastic (e.g., PEEK), a second cage comprising a biocompatible plastic (e.g., PEEK), and a flexible elastomer sandwiched between the first and second cages. The first and second lateral surfaces of the first cage and the second cage may each have the contact area configured to engage the portion of the vertebrae exposed by the corpectomy. In addition, the first and second cages may each define an open graft area extending from the first lateral surface to the second lateral surface suitable for receiving bone graft material.

BRIEF DESCRIPTION OF DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Figure 1:
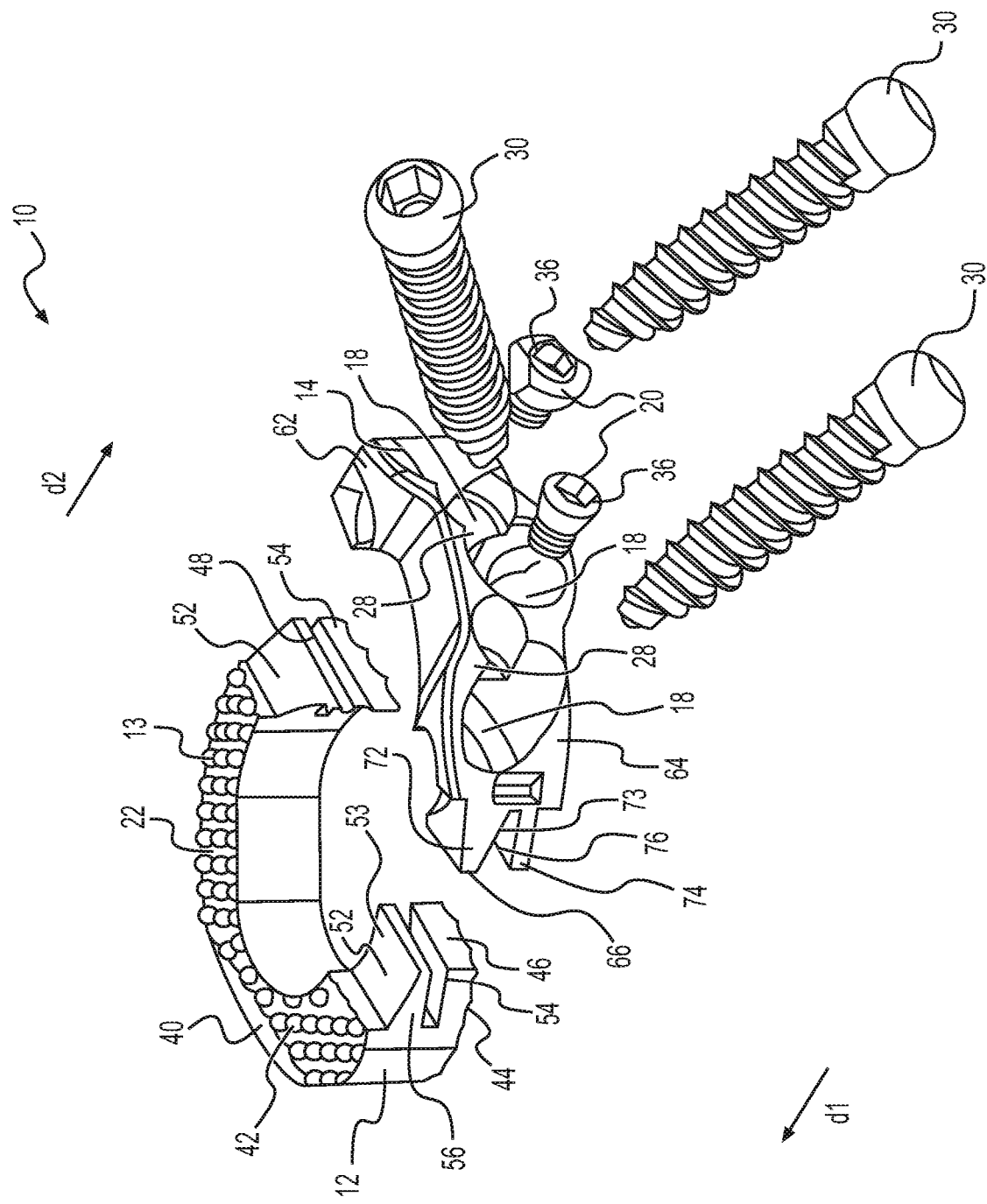
FIG. 1 is an exploded view of one embodiment of an intervertebral implant including a spacer and a plate.

Embodiments of the disclosure are generally directed to stand-alone interbody fusion implants and corpectomy implants suitable for use with oblique implantation. Specifically, the implants are designed to allow for an oblique or anterolateral approach to the spine, including the lumbar and cervical spine. In particular, the implants may be inserted in an oblique direction, e.g., at an angle of about 45° with respect to the mid-sagittal plane. By providing this oblique or anterolateral approach, no dissection of the vessels in front of the vertebrae is required and contact with the vascular anatomy of the patient can be avoided or minimized.

Certain embodiments may be used on the cervical, thoracic, lumbar, and/or sacral segments of the spine. For example, the size and mass increase of the vertebrae in the spine from the cervical to the lumbar portions is directly related to an increased capacity for supporting larger loads. This increase in load bearing capacity, however, is paralleled by a decrease in flexibility and an increase in susceptibility to strain. When rigid immobilization systems are used in the lumbar segment, the flexibility is decreased even further beyond the natural motion restriction of that segment. Replacing the conventional rigid immobilization systems with certain embodiments disclosed herein may generally restore a more natural movement and provide added support to the strain-susceptible areas.

As used herein and in the claims, the terms "comprising" and "including" are inclusive or open-ended and do not exclude additional unrecited elements, compositional components, or method steps. Accordingly, the terms "comprising" and "including" encompass the more restrictive terms "consisting essentially of" and "consisting of."

FIGS. 1-8 illustrate different views of one particular embodiment of the stand-alone intervertebral implant 10. As shown in the exploded view of FIG. 1, the implant 10 includes a spacer 12 and a plate 14. The spacer 12 includes a superior surface 42 and an inferior surface 44. The superior and inferior surfaces 42, 44 each have a contact area 22 configured to contact and engage adjacent vertebrae 80. The spacer 12 has a curved or substantially U-shaped body with a first end 46 and a second end 48. The plate 14 has an upper surface 62, a lower surface 64, an anterior surface 65, a first end 66, a second end 68, and at least one bore or screw hole 18 traversing the plate 14 for receiving a screw 30. The plate 14 is affixed to the spacer 12. In particular, the plate 14 is coupled to the spacer 12 where the first end 46 of the spacer 12 engages or joins the first end 66 of the plate 14 and the second end 48 of the spacer 12 engages or joins the second end 68 of the plate 14.

Figure 2:
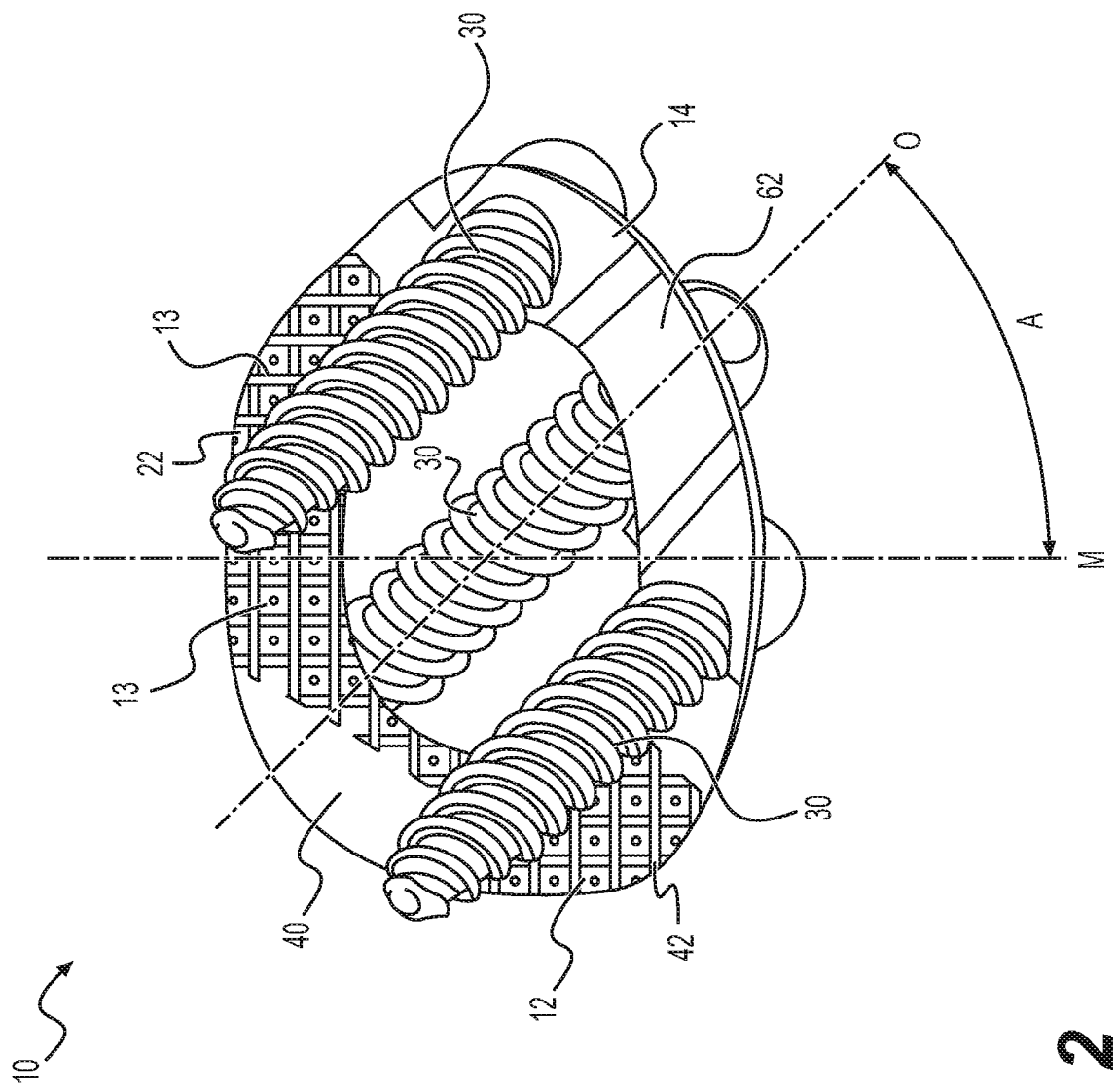
FIG. 2 is a top view of the intervertebral implant depicted in FIG. 1 once assembled.

As is evident in FIG. 2, the implant 10 is asymmetrical such that a median plane M divides the spacer 12 and the plate 14 into two asymmetrical halves. In addition or in the alternative, the implant 10 may be asymmetrical such that an oblique plane O divides the spacer 12 and the plate 14 into two asymmetrical halves. As used herein, asymmetrical is intended to encompass an implant 10 lacking symmetry from side-to-side along either or both the median plane M and the oblique plane O when viewed from a top elevation, for example, as provided in FIG. 2. In other words, the median plane M and/or the oblique plane O bisect the implant 10 into two parts that are not identical or mirror images of one another.

Figure 6:
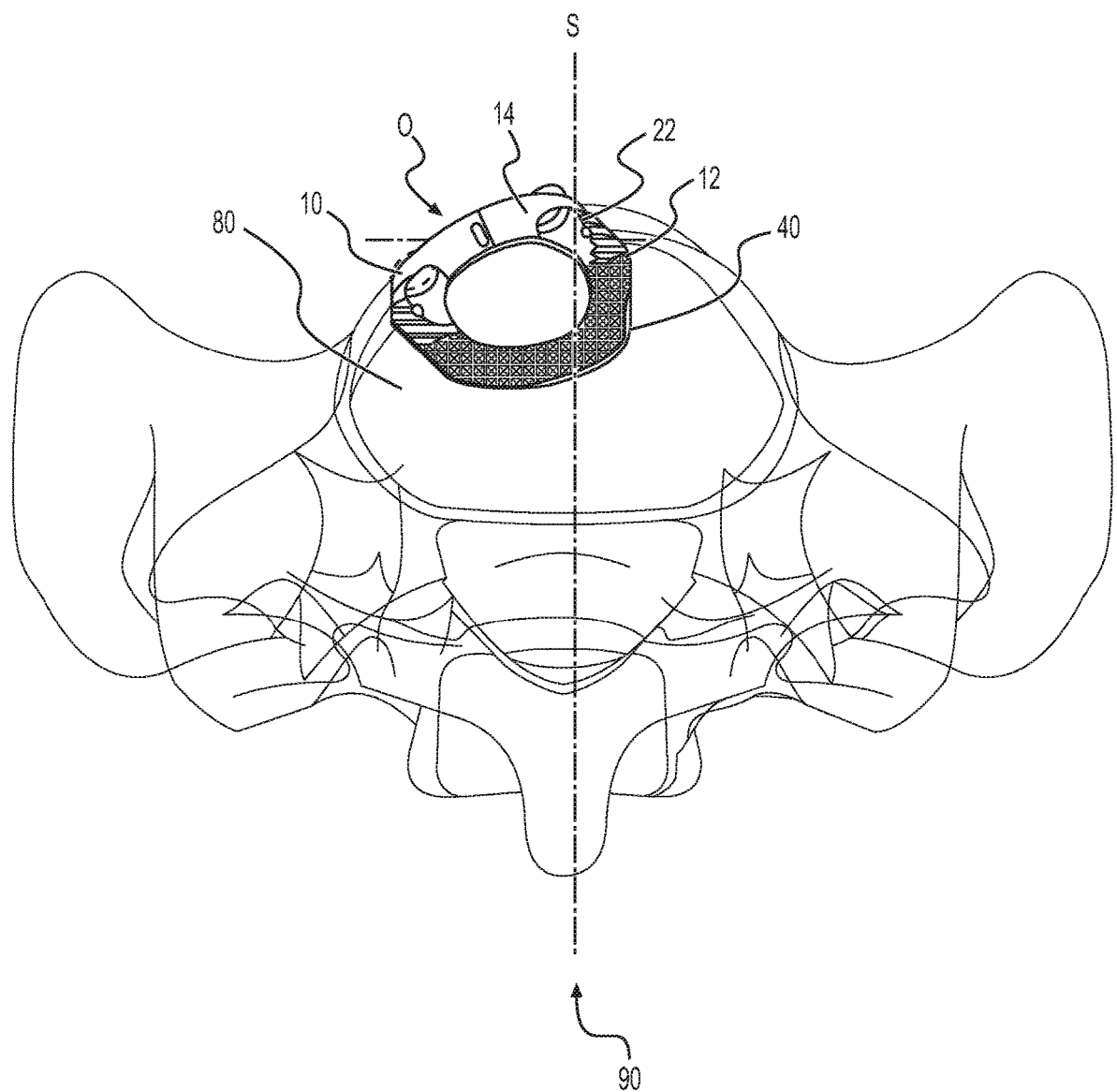
FIG. 6 is a top view of the portion of the spine depicted in FIG. 5 with the intervertebral implant depicted in FIG. 4 implanted between adjacent vertebrae.

The asymmetrical nature of the implant 10 may allow for an oblique or anterolateral approach to the spine (e.g., lumbar, cervical). In particular, the implant 10 may be inserted in an oblique direction along the oblique plane O. As shown in FIGS. 2 and 6, the oblique plane O may be at an angle A relative to the mid-sagittal plane S (e.g., the same as the median plane M). The angle A may be an angle of about 45° with respect to the mid-sagittal plane S and/or the median plane M. For example, the angle A may range from about 10° to about 80°, about 25° to about 65°, about 35° to about 55°, or about 40° to 50° with respect to the mid-sagittal plane S and/or the median plane M. This approach by a surgeon can minimize the contact with the vascular anatomy and need to dissect vessels in front of the vertebrae, which is necessary with an anterior approach.

The implant 10 may be asymmetrical based on different configurations of the plate 14 and the spacer 12. The spacer 12 has a curved, C-shaped, or substantially U-shaped body, which may be asymmetrical along the median plane M, the oblique plane O, or both planes. The plate 14 may also have a curved, C-shaped, or substantially U-shaped body, which also may be asymmetrical along the median plane M, the oblique plane O, or both planes. Thus, the plate 14, the spacer 12, or both of the plate 14 and the spacer 12 may be independently asymmetrical. The shape of the spacer 12 and the plate 14 may also be asymmetrical in that the curve is not consistent. In other words, the curved body for each of the spacer 12 and the plate 14 may be skewed from a normal or symmetric curve. In addition, the perimeter of the curved body for each of the spacer 12 and the plate 14 may contain flat or angled segments along the perimeter or periphery of the implant 10.

As is evident in FIGS. 1 and 2, the plate 14 may be asymmetrical along the oblique plane O such that the first end 66 of the plate 14 extends a distance d1 beyond the second end 68 of the plate 14. In other words, the distance d1 is a relative distance between the length of the first end 66 of the plate 14 less the length of the second end 68 of the plate 14. In a corresponding manner, the spacer 12 may be asymmetrical along the oblique plane O where the second end 48 of the spacer 12 extends a distance d2 beyond the first end 46 of the spacer 12. Thus, the first and second ends 66, 68 of the plate 14 are not equivalent or uniform. Again, the distance d2 is a relative distance between the length of the second end 48 of the spacer 12 less the length of the first end 46 of the spacer 12. The first and second ends 46, 48 of the spacer 12 are also not equivalent. Although not shown, the distance, length, or configuration of the ends or any portion of the plate 14 or the spacer 12 may be reversed or modified as would be appreciated by one of ordinary skill in the art to provide an asymmetrical implant 10 especially appropriate for insertion and implantation along the oblique plane O.

The spacer 12 may further include a leading taper 40 for ease of insertion. The leading taper 40 may be in the form of a chamfer or a bevel which enables self-distraction of the vertebral bodies 80 during insertion of the implant 10. The leading taper 40 may be located along the insertion direction of the implant 10 (e.g., along the oblique plane O). In the case of an oblique insertion direction, the leading taper 40 is positioned asymmetrically on the spacer 12 with respect to the median plane M. In addition, the leading taper 40 may be asymmetrically positioned such that the leading taper 40 also crosses or intersects the oblique plane O. As shown in FIG. 2, the leading taper 40 may intersect the oblique plane O, but the oblique plane O does not necessarily need to bisect the leading taper 40 into equal parts. The leading taper 40 may correspond to the angle A, which may range from about 10° to about 80°, about 25° to about 65°, about 35° to about 55°, about 40° to 50°, or about 45%, for example.

The spacer 12 and the plate 14 may be coupled, removably coupled, connected, or attached together in any suitable manner known in the art. The spacer 12 and the plate 14 may also be coupled together through appropriate coupling means or fasteners. Portions of the spacer 12 and the plate 14 may be assembled together using, alone or in combination, a friction fit, a dovetail assembly, dowel pins, hooks, staples, screws, adhesives, and the like, or any suitable fasteners known in the art, which can be used to permanently attach the spacer 12 and the plate 14 together. The implant 10 is in the form of a stand-alone fusion device to provide structural stability and a low or zero profile design. The implant 10 is preferably assembled before insertion into the disc space.

Figure 3:
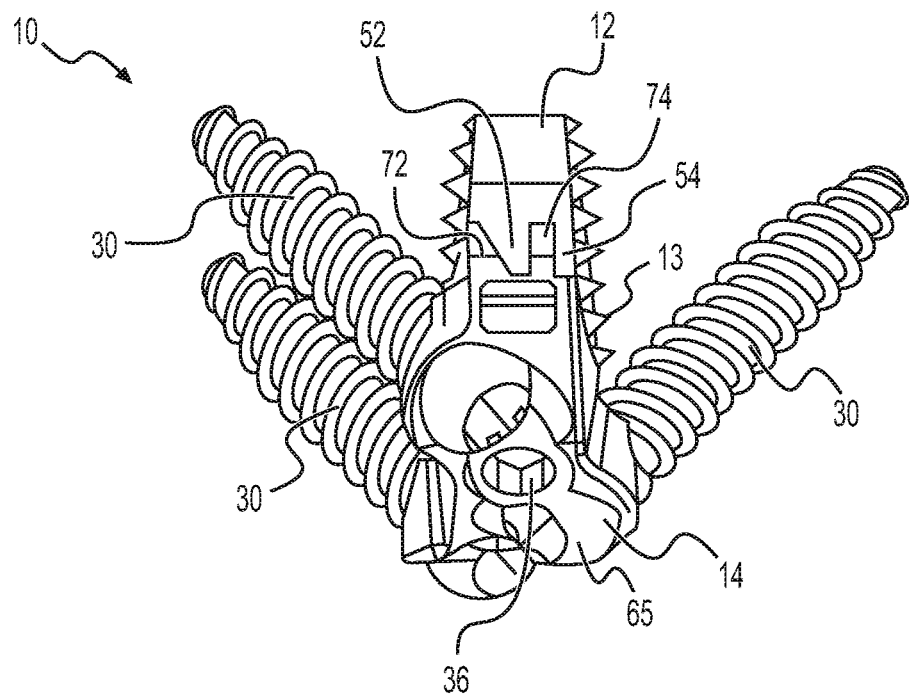
FIG. 3 is a side view of the intervertebral implant provided in FIG. 2.
Figure 4:
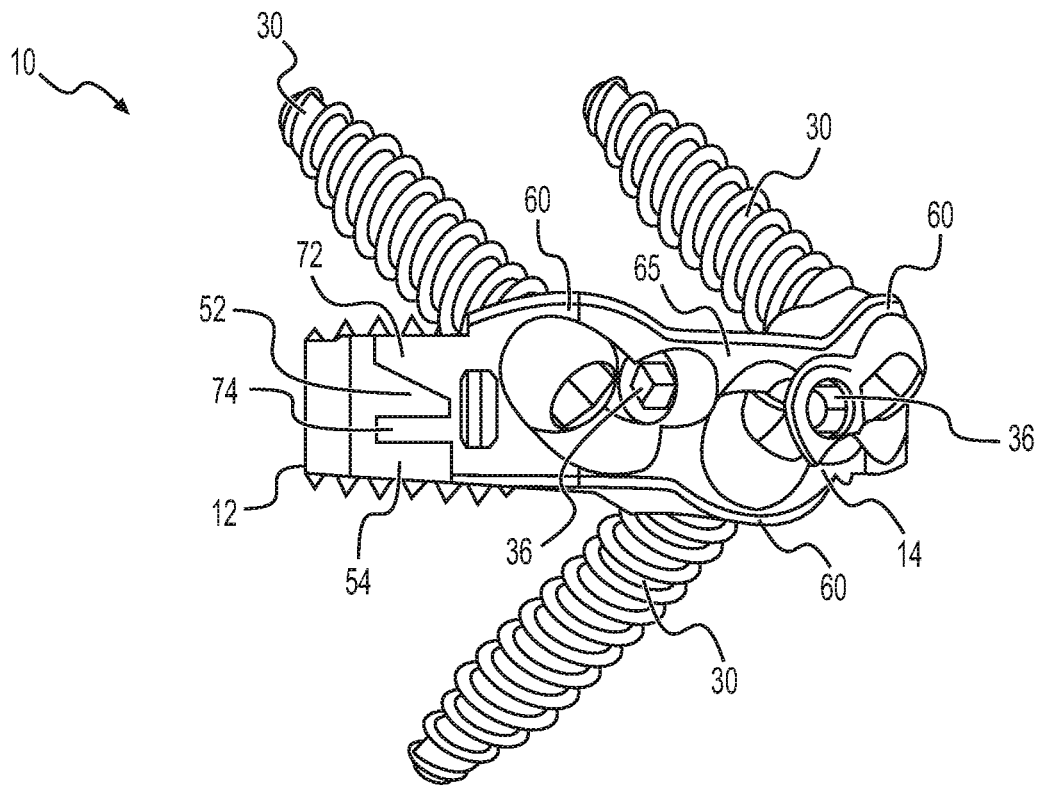
FIG. 4 is an alternative side view of the intervertebral implant depicted in FIG. 3.
Figure 7:
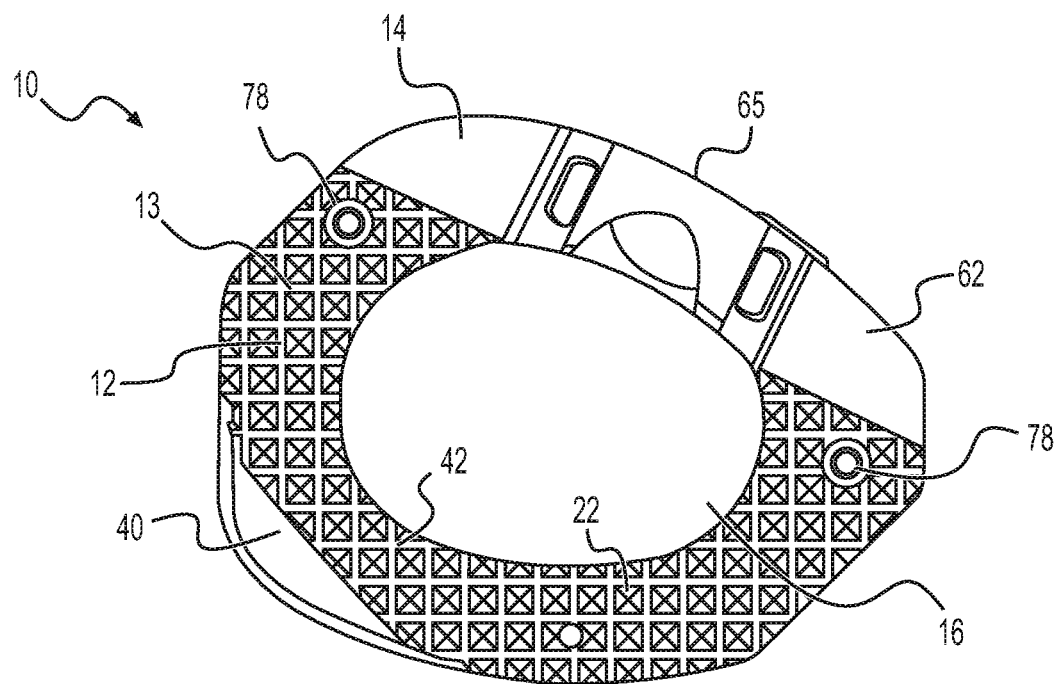
FIG. 7 depicts a top view of the intervertebral implant depicted in FIG. 4.

According to one embodiment shown in FIGS. 3 and 4, the first and second ends 46, 48 of the spacer 12 may be attached to the first and second ends 66, 68 of the plate 14 in the form of a friction fit assembly with or without pins 78 (shown in FIG. 7). For example, the first and second ends 46, 48 of the spacer 12 each comprise first and second projections 52, 54 with a recess 56 defined therebetween. The first and second ends 66, 68 of the plate 14 also each comprise first and second projections 72, 74 with a recess 76 defined therebetween. At least one of the first and second projections 52, 54 of the spacer 12 or the first and second projections 72, 74 of the plate 14 is matingly received in the corresponding recess 56 of the spacer or the recess 76 of the plate 14. For example, the second projections 74 of the plate 14 may be dovetailed or friction fit within the recesses 56 of the spacer 12 or the second projections 54 of the spacer 12 may be dovetailed or friction fit within the recesses 76 of the plate 14. The first projections 52 of the spacer 12 may be received within the recess 76 of the plate 14 or the first projections 72 of the plate 14 may be received within the recess 56 of the spacer 12.

In the embodiment shown in FIGS. 1-4, the second projections 74 of the plate 14 are received within the recesses 56 of the spacer 12 and the first projections 52 of the spacer 12 are received with the recesses 76 of the plate 14 to couple the spacer 12 and the plate 14 together. In addition, the first projections 52 of the spacer 12 may include a sloped upper surface 53. The first projections 72 of the plate 14 may include a sloped lower surface 73. The sloped upper surface 53 of the first projections 52 of the spacer 12 may therefore correspond and mate with the sloped lower surface 73 of the first projections 72 of the plate 14 to further secure the first end 46 of the spacer 12 to the the first end 66 of the plate 14 and the second end 48 of the spacer 12 to the second end 68 of the plate 14.

In addition or in the alternative, as shown in FIG. 7, the spacer 12 and the plate 14 may be secured together with pins 78 which traverse at least a portion of the spacer 12 and/or the plate 14 at a position proximate to either or both of the first and second ends 46, 48 of the spacer 12 and the first and second end 66, 68 of the plate 14. These pins 78 may pass through holes (not shown), for example, in a substantially perpendicular manner relative to a horizontal plane. For example, the pins 78 may be oriented substantially perpendicular relative to the superior and/or inferior surfaces 42, 44 of the spacer 12 and/or the upper and/or lower surfaces 62, 64 of the plate 14. The pins 78 may pass through the first and second projections of the 52, 54 of the spacer 12 and the first and second projections 72, 74 of the plate 14. The pins 78 may be in the form of dowels formed from a biocompatible material, such as titanium, or the pins 78 may be formed from tantalum, for example, to enable radiographic visualization.

Figure 5:
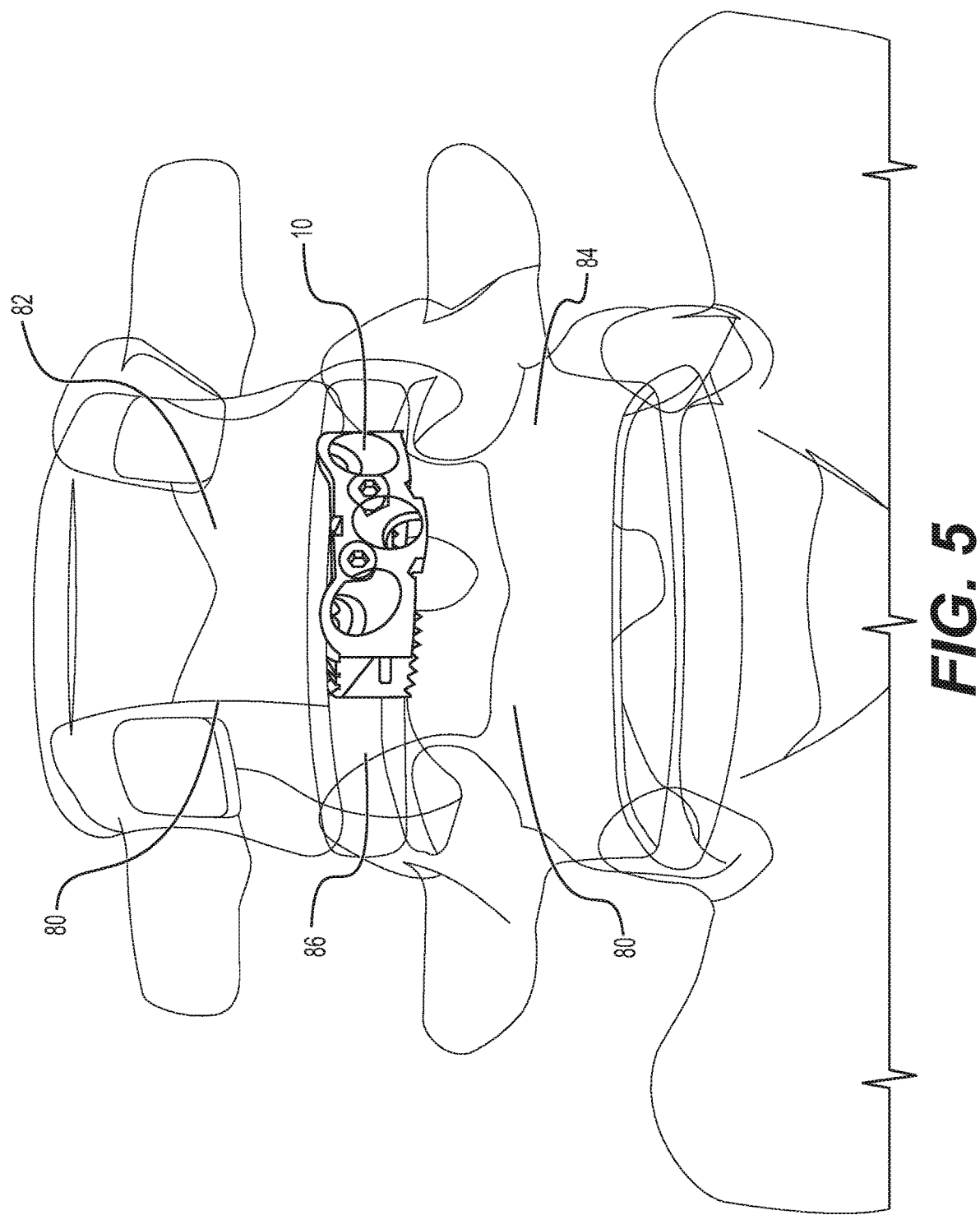
FIG. 5 is an anterior view of a portion of lumbar spine with the intervertebral implant depicted in FIG. 4 implanted between adjacent vertebrae.

As depicted in FIG. 5, the intervertebral implant 10 may be implanted in an intervertebral space 86 between adjacent vertebrae 80. In particular, the implant 10 may be implanted in the intervertebral space 86 between a first superior vertebra 82 and a second inferior vertebra 84. In order to engage the adjacent vertebrae 80, the spacer 12 may include a plurality of protrusions 13 or teeth on the contact areas 22 of the superior and/or inferior surfaces 42, 44. The protrusions 13 on the superior and inferior surfaces 42, 44 of each implant 10 grip the endplates of the adjacent vertebrae 80, resist migration, and aid in expulsion resistance. The plurality of protrusions 13 may be pyramidal in shape, but the protrusions 13 can be configured to be any size or shape to enhance anchoring the spacer 12 and the implant 10 to each of the adjacent vertebrae 80.

The implant 10 may also contain an opening 16 configured for receiving bone graft material to promote fusion of the adjacent vertebral bodies 80. Unlike a traditional spacer having an opening for receiving graft materials where the spacer completely surrounds or envelops the graft retaining area, the spacer 12, as shown in FIG. 1, for example, has a curvature to match the vertebral endplate 80. In particular, the spacer 12 has a substantially U-shaped body with a completely open portion defined between the first and second ends 46, 48. It is only when the spacer 12 and plate 14 are coupled together that the plate 14 closes the open portion of the spacer 12. It is the combination of the spacer 12 and the plate 14 together that defines the inner void or open graft area 16. In other words, the perimeter of the U-shaped spacer 12 and the perimeter of the plate 14 together define the inner void or open area 16. The open graft area 16 may extend from the superior surface 42 to the inferior surface 44 of the spacer 12 to define a substantially hollow center suitable for retaining one or more bone graft materials.

The intervertebral implant 10 may be positioned in the spine after the disc portion between the two vertebral bodies 80 is exposed and removed, for example, using rongeurs or other suitable instruments. The posterior and lateral walls of the annulus are generally preserved to provide peripheral support for the implant 10 and graft materials. A trial device attached to a trial holder may then be inserted into the disc space 86 to determine size of the implant 10. This procedure is generally conducted using fluoroscopy and tactile feel. The implant 10 may be available in various heights and geometric options to fit the anatomical needs of a wide variety of patients. After the appropriate sized implant 10 is selected and attached to an implant holder and drill guide (not shown), the implant 10 may be inserted into the disc space 86. Before or after the implant 10 is positioned within the disc space 86, supplemental graft material can be used to enhance fusion. The implant 10 may be implanted in the vertebral space 86 using an oblique, anterolateral, anterior, posterior, lateral, and/or transforaminal approach.

The implant 10 is preferably implanted in the vertebral space 86 using an oblique or anterolateral approach. FIG. 6 depicts a top view of of the portion of the lumbar spine including the anterior side 88 and the posterior side 90, with the intervertebral implant 10 implanted between adjacent vertebrae 80. As shown, the implant 10 may be placed in the lumbar spine in an oblique direction along the oblique plane O. The oblique plane O may be at an angle A relative to the mid-sagittal plane S. The angle A may be about 45° with respect to the mid-sagittal plane S. The asymmetrical nature of the implant 10 allows for this oblique or anterolateral approach to the lumbar spine and oblique positioning between the adjacent vertebrae 80. Although depicted on the left side in the quadrant proximate to the anterior side 88 of the vertebra 80, a similar oblique approach may be taken to position the implant 10 on the right side in the quadrant opposite to the mid-sagittal plane S of the vertebrae 80. When fully inserted, the implant 10 can be fully contained within the disc space 86 to provide for a zero-profile in regard to the anterior and lateral aspects of the spinal column. In particular, the implant 10 does not extend beyond the anterior face 88 or lateral side of the vertebrae 80.

The implant 10 may be secured to the adjacent vertebrae 80 in any suitable manner known in the art. The implant 10 may be secured with fasteners, screws, pins, nails, or the like. As shown in FIGS. 3 and 4, the plate 14 of the implant 10 may be secured to the adjacent vertebrae 80 using one or more screws 30. The plate 14 includes one or more screw holes 18 to receive the screws 30. The screw holes 18 are configured to receive the screws 30 at various angles. The screw holes 18 for receiving the screw 30 may traverse the anterior surface 65 of the plate 14 at an angle divergent to a horizontal plane in order to secure the implant 10 to one or both of the adjacent vertebrae 80. Thus, the screws 30 enter the screw holes 18 at specified angles to enter the adjacent vertebrae 80 at the optimal locations. For example, the screws 30 may be aligned so that they anchor into the apophyseal rings of two adjacent vertebral bodies 80.

Figure 8:
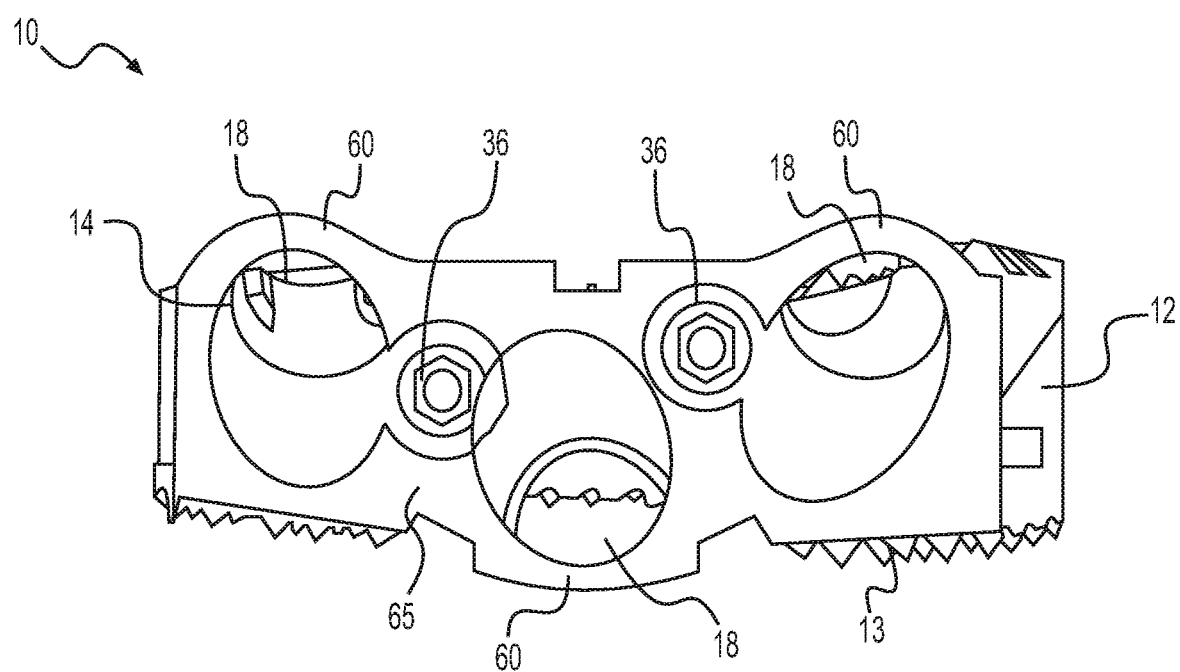
FIG. 8 provides a front view of the intervertebral implant depicted in FIG. 4.

The anterior surface 65 of the plate 14 may also include one or more eyebrows 60 projecting past or beyond the upper or lower surfaces 62, 64 of the plate 14 providing passage for one or more angled screw holes 18 designed to accommodate one or more angles screws 30. As shown in FIG. 8, the anterior surface 65 of the plate 14 may include two eyebrows 60 extending beyond the upper surface 62 of the plate 14 to accommodate two angled screw holes 18, which are retaining two angled screws 30 configured to secure the implant 10 into the superior vertebra 82. The plate 14 also includes one eyebrow 60 extending below the lower surface 64 of the plate 14 to accommodate one angled screw hole 18, which is retaining a single angled screws configured to secure the implant 10 into the inferior vertebra 84. The eyebrows 60 may be rounded and smooth or notched. Although depicted with three screws 30 and with two eyebrows 60 extending beyond the upper surface 62 and one eyebrow extending beyond the lower surface 64, the eyebrows 60 and positioning of the screws 30 may be modified to accept any suitable number and configuration of screws 30 needed to secure the implant 10 to the adjacent vertebrae 80.

Once the implant 10 is positioned inside the disc space 86, an awl or any similar type of instrument, for example, can be used to drill through the screw hole 18 and break the cortex of the adjacent vertebral body 80. The surgeon performing this procedure may then use a depth gauge to determine the screw length. Once the appropriate screw length is determined, screws 30 may be inserted using a self-retaining screwdriver, for example. Any suitable type of screw 30 may be selected by one of ordinary skill in the art. For example, the screws 30 may include fixed or variable angle screws of any suitable size with appropriate thread spacing, thread pitch, head design, length, and the like.

Once inserted, the screws 30 may be secured with an anti-back out prevention or locking mechanism 20. As depicted in FIG. 1, the locking mechanism 20 may be disposed on the plate 14 (e.g., the anterior surface 65) for preventing back out of the screws 30. For example, a cam-style blocking mechanism may be used with screws 36 that capture the fixation device screws 30 once they are inserted fully into the plate 14. One or more screw holes 28 may be provided on the anterior surface 65 of the plate 14, which at least partially overlap with the screw holes 18. As shown, the anti-back out mechanism 20 may include two set screws 36 that retain the screws 18 with the implant 10, although any suitable anti-back out mechanism 20 may be selected by one of ordinary skill in the art.

The plate 14 and spacer 12 may be comprised of any suitable material. The spacer 12 can be comprised of any material that is conducive to the enhancement of fusion between the two adjacent vertebrae 80. In one particular embodiment, the spacer 12 is made of a biocompatible plastic, like polyether ether ketone (PEEK), polyetherketoneketone (PEKK), ultra-high molecular weight (UHMW) polyethylene, or other polymers and plastics known in the art which are physiologically compatible. Any other materials that are physiologically compatible may also be used such as bone or metal. The plate 14 can also be comprised of any physiologically compatible material. In the preferred embodiment, the plate 14 is composed of a biocompatible metal, such as stainless steel, titanium, titanium alloys, surgical steel, and metal alloys, for example. Preferably, the plate is formed from titanium or a titanium alloy. Any other materials that are physiologically compatible may also be used such as bone or plastic.

According to one embodiment, the multi-part low or zero-profile implant 10 is configured to be positioned in between the vertebral bodies 80. A PEEK spacer 12 is provided that is configured to be attachable to a titanium plate 14. The PEEK spacer 12 is further provided with a curvature to match the vertebral endplate 80, a leading taper 40 for ease of insertion and teeth or protrusions 13 on the superior and inferior surfaces 42, 44 that engage with the endplates of the adjacent vertebral bodies 80 to resist migration. There is also provided a through hole 16 that extends from the superior surface 42 to the inferior surface 44 of the spacer 12 for receiving bone graft material to promote fusion of the adjacent vertebral bodies 80.

The titanium plate 14 is provided with bore holes 18 that are configured to accept fastening devices, such as screws 30 for fixation to the vertebral bodies 80. It should be noted that rather than screws, pins or nail type devices may also be used. The bore holes 18 are aligned so that they anchor into the apophyseal rings of the two adjacent vertebral bodes 80 for increased fixation. In this particular embodiment, the cam-style blocking mechanism 20 is provided. Specifically, the cam-style blocking mechanism 20 comprises screws 36 that when turned capture the fixations devices or screws 30 once they are inserted fully into the plate 14. The shape of the implant 10 is configured so that an anterior, oblique, anterolateral, lateral, and/or transforaminal approach may be used in positioning the plate 14 and the spacer 12 in the intervertebral space 86. When the implant 10 is fully inserted, the implant 10 will be contained within the disc space 86 and will have a zero profile with regard to the anterior and lateral aspects of the spinal column.

Figure 9:
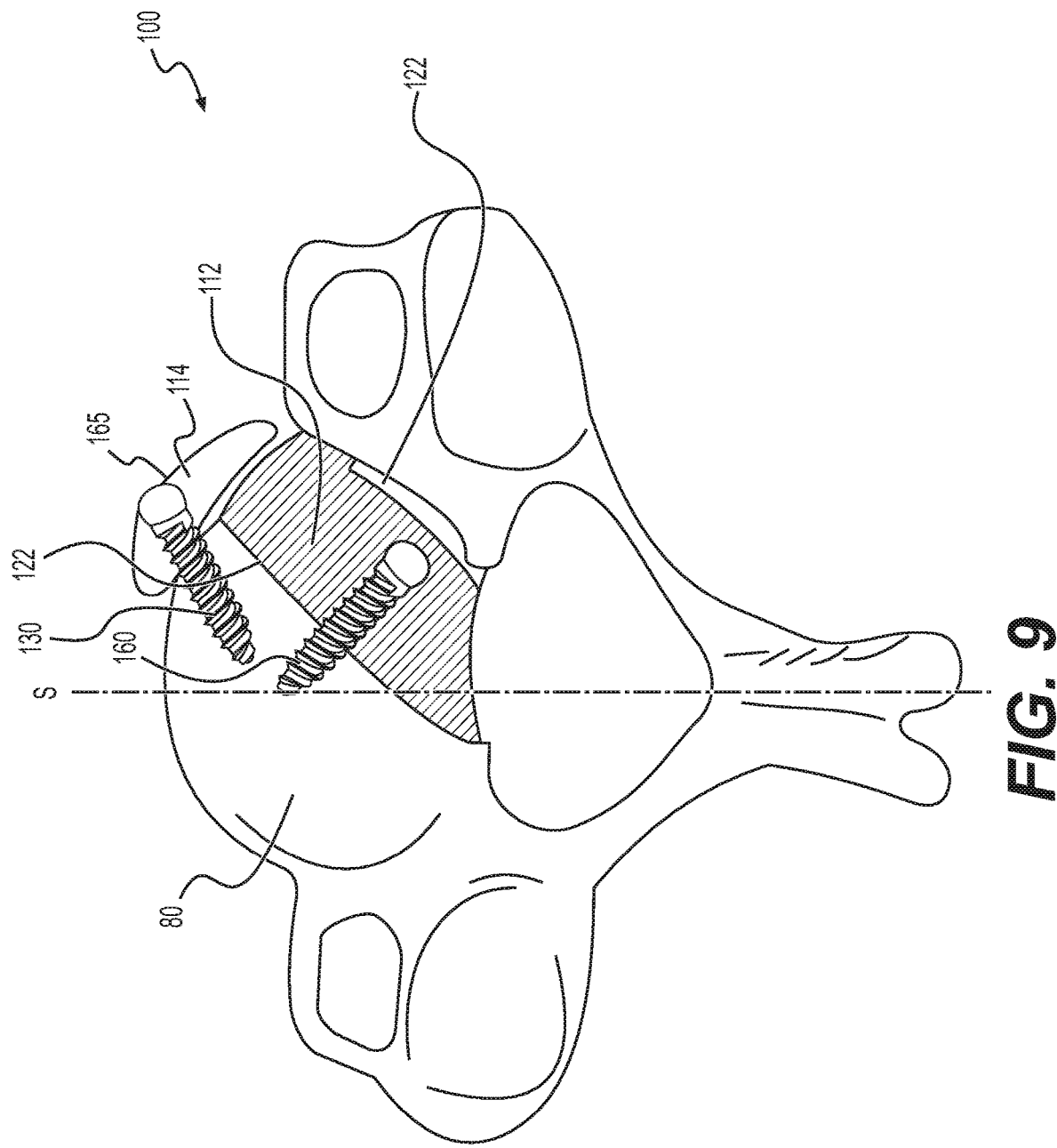
FIG. 9 is a top view of a portion of the cervical spine of another embodiment with an oblique corpectomy implant including a spacer and a plate.
Figure 10:
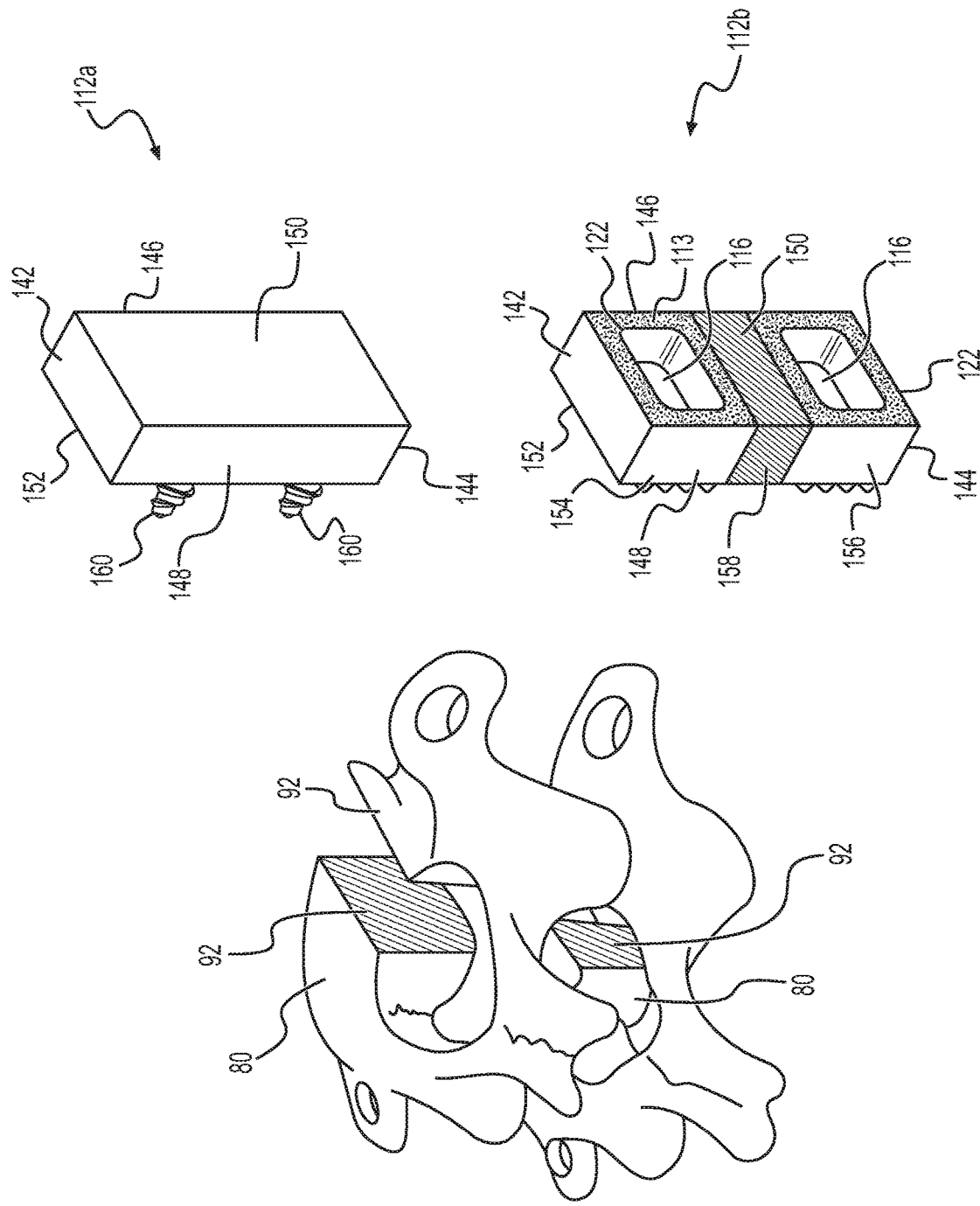
FIG. 10 is a perspective view of a portion of the cervical spine and two alternative spacers suitable for use with an oblique corpectomy.

According to another embodiment, as illustrated in FIGS. 9 and 10, there is provided an oblique spacer 112 that may be used as a corpectomy device. Specifically, a multi-level corpectomy implant 100 includes a spacer 112 for implantation in at least a portion of at least one vertebrae 80 and in an intervertebral space 86 between adjacent vertebrae 80. The spacer 112 includes a superior surface 142, an inferior surface 144, a first lateral surface 150, a second lateral surface 152, a front surface 146, and a rear surface 148. The first and second lateral surfaces 150, 152 each have at least one contact area 122 configured to engage a portion 92 of the vertebrae 80 exposed by a corpectomy. The spacer 112 is also configured to extend in the intervertebral space 86 between at least two adjacent vertebrae 80. The spacer 112 is shaped and configured to allow for an oblique or anterolateral approach (e.g., at an angle of about 45° with respect to the mid-sagittal plane S).

The spacer 112 may include at least one attachment mechanism to secure the spacer 112 to the portions 92 of the vertebrae 80 exposed by the corpectomy. FIG. 10 depicts two embodiments for the spacer 112a, 112b. For example, the attachment mechanism may include one or more fasteners, screws, pins, or the like. As shown in the spacer 112a, screws or pins 160 on the second lateral surface 152 and/or the first lateral surface 150 (not shown) may be provided to secure the spacer 112a to the portions 92 of the vertebrae 80 exposed by the corpectomy. In addition or in the alternative, as shown in the spacer 112b, the attachment mechanism may include a plurality of protrusions 113 on the contact areas 122 of the first and second lateral surfaces 150, 152 for engaging the portions 92 of the vertebrae 80 exposed by the corpectomy.

The corpectomy implant 100 may further include at least one plate 114. The one or more plates 114 may be coupled to a portion of the front surface 146 of the spacer 112. The plate 114 has an anterior surface 165 and at least one screw hole 118 traversing through the anterior surface 165 for receiving a screw 130 to secure the plate 114 to one of the adjacent vertebrae 80. The plate 114 may be of any suitable size, shape, or configuration as would be recognized by one of ordinary skill in the art. In one embodiment, the implant 100 may include two plates 114: a first plate 114 coupled to a first portion of the front surface 146 of the spacer 112 (e.g., in the region near the superior surface 142 proximate to a first vertebra 80) and a second plate 114 coupled to a second portion of the front surface 146 of the spacer 112 (e.g., in the region near the inferior surface 144 proximate to the second vertebra 80). Thus, the first plate 114 may secure the spacer 112 to a first vertebral body 80 and the second plate 114 may secure the spacer 112 to a second vertebral body 80, for example, using one or more screws 130.

The plate 114 and the spacer 112 may be comprised of any suitable material. FIG. 10 depicts two embodiments for the spacer 112a, 112b. For example, the spacer 112a may be formed from a flexible elastomer. Suitable elastomers may include, for example, polyurethanes, silicones, hydrogels, collagens, hyalurons, cryogels, proteins and other synthetic polymers that are configured to have a desired range of elastomeric mechanical properties, such as a suitable compressive elastic stiffness and/or elastic modulus. The elastomer is flexible in that it may be slightly flexed or bent, but the elastomer returns to its original shape.

The spacer 112b may include a multi-component body including a biocompatible plastic and a flexible elastomer. Biocompatible plastics may include polyetheretherketone (PEEK), polyetherketoneketone (PEKK), ultra-high molecular weight (UHMW) polyethylene, or other polymers and plastics known in the art which are biocompatible. The flexible elastomers include the same elastomers as discussed above. Specifically, the spacer 112b may include a multi-component body including a first cage 154 made from a biocompatible plastic (e.g., PEEK), a second cage 156 comprising a biocompatible plastic (e.g., PEEK), and a connector portion 158 comprising a flexible elastomer sandwiched between the first and second cages 154, 156. The first and second lateral surfaces 150, 152 of the first cage 154 and the second cage 156 may each contain the contact area 122 configured to engage the portions 92 of the vertebrae 80 exposed by the corpectomy. In addition, the first and second cages 154, 156 may each define an open graft area 116 extending from the first lateral surface 150 to the second lateral surface 152 suitable for receiving bone graft material. The implants 100 may be available in various heights and geometric options to fit the anatomical needs of a wide variety of patients.

These implants 10, 100 are specially designed to allow for an oblique or anterolateral approach to the spine (e.g., lumbar, cervical). In particular, the implants 10, 100 may be inserted in an oblique direction with respect to the mid-sagittal plane S. By providing access to the spine with this oblique or anterolateral approach, no dissection of the vessels in front of the vertebrae is required and contact with the vascular anatomy of the patient can be avoided or minimized. The shape and configuration of the implants 10, 100 are particularly suitable for the oblique approach based on the asymmetrical nature of the implant 10 and the oblique spacer 112 design of the corpectomy implant 100.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

We claim:

1. An intervertebral implant for implantation in an intervertebral space between adjacent vertebrae, the implant comprising:
    a spacer having a superior surface, an inferior surface, a first end, and a second end, wherein the inferior surface and the superior surfaces each have a contact area configured to engage adjacent vertebrae; and
    a plate having an upper surface, a lower surface, a first end, a second end, and at least one angled hole traversing the plate for receiving a fastener, wherein the plate has an anterior surface comprising at least one eyebrow projecting past the upper or lower surfaces and configured to provide passage for the at least one angled hole;
    a fastener for extending through the at least one angled hole;
    wherein the plate is coupled to the spacer in an assembled configuration such that the first end of the spacer engages the first end of the plate and the second end of the spacer engages the second end of the plate, wherein the implant is asymmetrical when the spacer is attached to the plate in the assembled configuration, wherein the implant is shaped such that no median plane divides the spacer and plate in the assembled configuration into two symmetrical sections
    wherein the plate and the spacer are configured and dimensioned to be positioned between adjacent vertebrae, wherein the at least one angled hole is angled so that the fastener can enter one of the adjacent vertebrae through an upper surface of the adjacent vertebral body and second and third fasteners can be secured to the other adjacent vertebrae through a lower surface of the adjacent vertebrae
    wherein a distance between the length of the second end of the spacer is less the length of the first end of the spacer, wherein the first and second ends of the spacer are also not equivalent in length,
    wherein the spacer and the plate are independently asymmetrical.

2. The implant of claim 1, wherein the implant is asymmetrical such that an oblique plane divides the spacer and the plate into two asymmetrical halves.

3. The implant of claim 2, wherein the plate is asymmetrical along the oblique plane where the first end of the plate extends a distance beyond the second end of the plate.

4. The implant of claim 2, wherein the spacer is asymmetrical along the oblique plane where the second end of the spacer extends a distance beyond the first end of the spacer.

5. The implant of claim 2, wherein the spacer comprises a leading taper asymmetrically positioned such that the leading taper crosses the oblique plane.

6. The implant of claim 1, wherein the plate has an asymmetrical curved body.

7. The implant of claim 1, wherein the implant is shaped and configured to allow for an oblique or anterolateral approach to the intervertebral space.

8. The implant of claim 1, wherein the first and second ends of the plate and the first and second ends of the spacer each comprise first and second projections with a recess defined therebetween, and wherein at least one of the first and second projections of the plate or the spacer are matingly received in the corresponding recess of the plate or the spacer.

9. The implant of claim 8, wherein the first projections of the spacer comprise a sloped upper surface which corresponds to a sloped lower surface of the first projections of the plate.

10. The implant of claim 8, wherein the second projection of the plate is friction fit within the recess of the spacer.

11. The implant of claim 1, wherein the at least one angled hole is configured to receive a second fastener which traverses the anterior surface of the plate at an angle divergent to a horizontal plane.

12. The implant of claim 1, wherein the spacer and the plate define an open graft area extending from the superior surface to the inferior surface of the spacer and configured to receive bone graft material.

13. The implant of claim 1, wherein the spacer includes a plurality of protrusions on the contact areas of the superior and inferior surfaces for engaging the adjacent vertebrae.

14. The implant of claim 1 further comprising a locking mechanism disposed on the plate for preventing back out of the fastener from the at least one angled hole.

15. The implant of claim 1, wherein the plate comprises a biocompatible metal.

16. The implant of claim 1, wherein the spacer comprises a biocompatible plastic.

17. An intervertebral implant for implantation in an intervertebral space between adjacent vertebrae, the implant comprising:

a spacer having a superior surface, an inferior surface, a first end, and a second end, wherein the inferior surface and the superior surfaces each have a contact area configured to engage adjacent vertebrae;

a plate having an upper surface, a lower surface, a first end, a second end, wherein the plate has an anterior surface comprising at least one eyebrow projecting past the upper or lower surfaces and at least one angled hole; and a fastener for extending through the at least one angled hole of the plate;

wherein the plate is attached to the spacer in an assembled configuration such that the first end of the spacer engages the first end of the plate and the second end of the spacer engages the second end of the plate, and wherein when viewed from a top elevation, the implant is shaped such that no median plane divides the spacer and the plate in the assembled configuration into two symmetrical sections;

wherein the plate and the spacer are configured and dimensioned to be positioned between adjacent vertebrae, wherein the at least one angled hole is angled so that the fastener can enter one of the adjacent vertebrae through an upper surface of the adjacent vertebral body and second and third fasteners can be secured to the other adjacent vertebrae through a lower surface of the adjacent vertebrae, wherein a distance between the length of the second end of the spacer is less the length of the first end of the spacer, wherein the first and second ends of the spacer are also not equivalent in length wherein the spacer and the plate are Independently asymmetrical.

* * * * *